US00PP25116P2

(12) United States Plant Patent
Bernuetz

(10) Patent No.: US PP25,116 P2
(45) Date of Patent: Nov. 25, 2014

(54) ***EUPHORBIA* PLANT NAMED 'BONPRI 635'**

(50) Latin Name: ***Euphorbia pulcherrima* Willd. ex Klotzsch×*Euphorbia cornastra***
Varietal Denomination: Bonpri 635

(71) Applicant: Andrew Bernuetz, Silverdale (AU)

(72) Inventor: Andrew Bernuetz, Silverdale (AU)

(73) Assignee: Bonza Botanicals Pty. Ltd., Yellow Rock, NSW (AU)

( * ) Notice: Subject to any disclaimer, the term of this patent is extended or adjusted under 35 U.S.C. 154(b) by 86 days.

(21) Appl. No.: 13/815,118

(22) Filed: Jan. 31, 2013

(51) Int. Cl.
*A01H 5/00* (2006.01)

(52) U.S. Cl.
USPC ..... Plt./304

(58) Field of Classification Search
USPC ..... Plt./302, 303, 304
See application file for complete search history.

*Primary Examiner* — Susan McCormick Ewoldt
(74) *Attorney, Agent, or Firm* — C. A. Whealy

(57) ABSTRACT

A new and distinct cultivar of *Euphorbia* plant named 'Bonpri 635', characterized by its compact, upright and mounded plant habit; moderately vigorous growth habit; freely branching habit; dark green-colored leaves; inflorescences with white-colored flower bracts with red purple-colored venation; and good post-production longevity.

1 Drawing Sheet

Botanical designation: *Euphorbia pulcherrima* Willd. ex Klotzsch×*Euphorbia cornastra.*

Cultivar denomination: 'BONPRI 635'.

BACKGROUND OF THE INVENTION

The present invention relates to a new and distinct cultivar of *Euphorbia* plant, an interspecific hybrid botanically known as *Euphorbia pulcherrima* Willd. ex Klotzsch×*Euphorbia cornastra*, and hereinafter referred to by the name 'Bonpri 635'.

The new *Euphorbia* plant is a naturally-occurring whole plant mutation of a proprietary selection of *Euphorbia pulcherrima* Willd. ex Klotzsch×*Euphorbia cornastra* 'Bonprilipcom', disclosed in U.S. Plant Pat. No. 21,327. The new *Euphorbia* plant was discovered and selected by the Inventor as a flowering plant from within a population of plants of the parent selection in a controlled greenhouse environment in Yellow Rock, New South Wales, Australia in June, 2007.

Asexual reproduction of the new *Euphorbia* plant by terminal vegetative cuttings in a controlled greenhouse environment in Yellow Rock, New South Wales, Australia since June, 2007 has shown that the unique features of this new *Euphorbia* plant are stable and reproduced true to type in successive generations of asexual reproduction.

SUMMARY OF THE INVENTION

Plants of the new *Euphorbia* have not been observed under all possible environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Bonpri 635'. These characteristics in combination distinguish 'Bonpri 635' as a new and distinct *Euphorbia* plant:

1. Compact, upright and mounded plant habit.
2. Moderately vigorous growth habit.
3. Freely branching habit.

4. Dark green-colored leaves.
5. Inflorescences with white-colored flower bracts with red purple-colored venation.
6. Good post-production longevity.

In side-by-side comparisons conducted in Yellow Rock, New South Wales, Australia, plants of the new *Euphorbia* differ primarily from plants of the parent, 'Bonprilipcom', in flower bract color as plants of 'Bonprilipcom' have pink-colored flower bracts.

Plants of the new *Euphorbia* can be compared to plants of the *Euphorbia pukherrima* Willd. ex Klotzsch×*Euphorbia cornastra* 'Bonpriho', disclosed in U.S. Plant Pat. No. 23,296. In side-by-side comparisons conducted in Yellow Rock, New South Wales, Australia, plants of the new *Euphorbia* differed from plants of 'Bonpriho' in the following characteristics:

1. Plants of the new *Euphorbia* were shorter than plants of 'Bonpriho'.
2. Plants of the new *Euphorbia* were not as vigorous as plants of 'Bonpriho'.
3. Plants of the new *Euphorbia* were more freely branching than plants of 'Bonpriho'.
4. Plants of the new *Euphorbia* had shorter internodes than plants of 'Bonpriho'.
5. Leaves of plants of the new *Euphorbia* were darker green in color than leaves of 'Bonpriho'.
6. Plants of the new *Euphorbia* and 'Bonpriho' differed slightly in flower bract color.

BRIEF DESCRIPTION OF THE PHOTOGRAPHS

The accompanying photographs illustrate the overall appearance of the new *Euphorbia* plant showing the colors as true as it is reasonably possible to obtain in colored reproductions of this type. Colors in the photographs may differ slightly from the color values cited in the detailed botanical description which accurately describe the colors of the new *Euphorbia* plant.

The photograph at the top of the sheet comprises a side perspective view of a typical flowering plant of 'Bonpri 635' grown in a container.

The photograph at the bottom of the sheet is a close-up view of a typical flowering plant of 'Bonpri 635'.

DETAILED BOTANICAL DESCRIPTION

Plants used in the aforementioned photographs and herewith described in detail were grown in 12-cm containers during the autumn in a polyethylene-covered greenhouse in Higashiomi, Shiga, Japan and under cultural practices typical of commercial production. During the production of the plants, day temperatures averaged 23° C. and night temperatures averaged 13° C. Measurements and numerical values represent averages for typical flowering plants. Plants were four months old when the photographs and the description were taken. In the following description, color references are made to The Royal Horticultural Society Colour Chart, Fourth Edition, 2007, except where general terms of ordinary dictionary significance are used.

Botanical classification: *Euphorbia pulcherrima* Willd. ex Klotzsch×*Euphorbia cornastra* 'Bonpri 635'.

Parentage: Naturally-occurring whole plant mutation of *Euphorbia pulcherrima* Willd. ex Klotzsch×*Euphorbia cornastra* 'Bonprilipcom', disclosed in U.S. Plant Pat. No. 21,327.

Propagation:

*Type*.—Terminal vegetative cuttings.

*Time to initiate roots, summer*.—About ten days at 18° C. to 25° C.

*Time to initiate roots, winter*.—About twelve days at 16° C. to 20° C.

*Time to produce a rooted young plant, summer*.—About three weeks at 18° C. to 25° C.

*Time to produce a rooted young plant, winter*.—About four weeks at 16° C. to 20° C.

*Root description*.—Fibrous; white in color.

*Rooting habit*.—Freely branching; medium density.

Plant description:

*Plant habit and form*.—Compact, upright and mounded plant habit; inverted triangle; inflorescences positioned above the foliar plane; moderately vigorous growth habit.

*Plant height*.—About 21.5 cm.

*Plant diameter or spread*.—About 28.3 cm.

*Lateral branch description*.—Branching habit: Freely branching habit, about six lateral branches develop per plant; pinching enhances lateral branch development. Length: About 14.8 cm. Diameter: About 3.6 mm. Internode length: About 2.8 cm. Aspect: Mostly upright. Strength: Strong. Texture: Smooth, glabrous. Color: Close to 144A.

*Foliage description*.—Arrangement: Alternate, simple. Length: About 9 cm. Width: About 5.4 cm. Shape: Ovate. Apex: Acute. Base: Truncate. Margin: Shallowly serrulate; undulate. Venation pattern: Pinnate, reticulate. Texture, upper and lower surfaces: Rugose, pubescent. Color: Developing leaves, upper surface: Close to 137A. Developing leaves, lower surface: Close to 137D. Fully developed leaves, upper surface: Close to 147A; venation, close to 144C. Fully developed leaves, lower surface: Close to N137D; venation, close to 144B. Petioles: Length: About 3 cm. Diameter: About 2.1 mm. Texture, upper and lower surfaces: Sparsely pubescent. Color, upper surface: Close to 137B tinted with close to N199A. Color, lower surface: Close to 138A.

Inflorescence description:

*Inflorescence type and habit*.—Inflorescences are compound corymbs of cyathia with colored flower bracts subtending the cyathia; inflorescences positioned above the foliage.

*Quantity of inflorescences*.—One inflorescence develops per lateral branch.

*Inflorescence diameter*.—About 13.5 cm.

*Inflorescence height*.—About 3.4 cm.

*Fragrance*.—None detected.

*Natural flowering season*.—Plants typically flower during the autumn and winter in Japan; inflorescence initiation and development can also be induced under artificial long nyctoperiod/short photoperiod conditions; early flowering habit, plants flower about 50 days under natural season conditions in Japan.

*Post-production longevity*.—Good post-production longevity; plants of the new *Euphorbia* maintain good substance and bract color for about seven weeks.

*Flower bracts*.—Quantity per inflorescence: About 24. Length, largest bracts: About 3.5 cm. Width, largest bracts: About 2.4 cm. Shape: Narrowly ovate to ovate. Apex: Acute. Base: Obtuse, rounded. Margin: Entire to serrulate; slightly undulate. Texture, upper and lower surfaces: Smooth, glabrous. Aspect: Mostly horizontal. Venation pattern: Pinnate, reticulate. Color: Developing or transitional bracts, upper surface: Close to NN155B, 65C and 143A. Developing or transitional bracts, lower surface: Close to 143C and 155C. Fully expanded bracts, immature, upper surface: Close to 155A; occasionally with random spots, close to 63A. Fully expanded bracts, immature, lower surface: Close to 155C. Fully expanded bracts, mature, upper surface: Close to NN155A; occasionally with random spots, close to 63A; venation, close to 63A. Fully expanded bracts, mature, lower surface: Close to NN155A; venation, close to 145C. Flower bract petioles: Length: About 1.2 cm. Diameter: About 1.1 mm. Texture, upper and lower surfaces: Smooth, glabrous. Color, upper and lower surfaces: Close to 145A.

*Cyathia*.—Quantity per corymb: About 20. Diameter of cyathia cluster: About 2.7 cm. Height, individual cyathium: About 6.2 mm. Diameter, individual cyathium: About 4.8 mm. Shape, individual cyathium: Globose. Color: Close to 144A. Nectaries: Quantity per cyathium: One. Size: About 2.7 mm by 3.8 mm. Color: Close to N144B.

*Peduncles*.—Length: About 2.8 mm. Diameter: About 1.5 mm. Strength: Strong. Aspect: Mostly upright. Texture: Smooth, glabrous. Color: Close to 145A.

*Reproductive organs*.—Stamens: Quantity per cyathium: Numerous. Anther shape: Lanceolate or globose. Anther length: About 0.3 mm to 0.7 mm. Anther color: Close to 154B. Amount of pollen: Scarce to none. Pollen color: Close to 155D. Pistils: Plants of the new *Euphorbia* have not been observed to develop pistils.

*Seeds and fruits*.—Seed and fruit production has not been observed on plants of the new *Euphorbia*.

Disease & pest resistance: Plants of the new *Euphorbia* have not been shown to be resistant to pathogens and pests common to *Euphorbia* plants.

Temperature tolerance: Plants of the new *Euphorbia* have been observed to tolerate temperatures ranging from about 8° C. to about 40° C.

It is claimed:

1. A new and distinct *Euphorbia* plant named 'Bonpri 635' as illustrated and described.

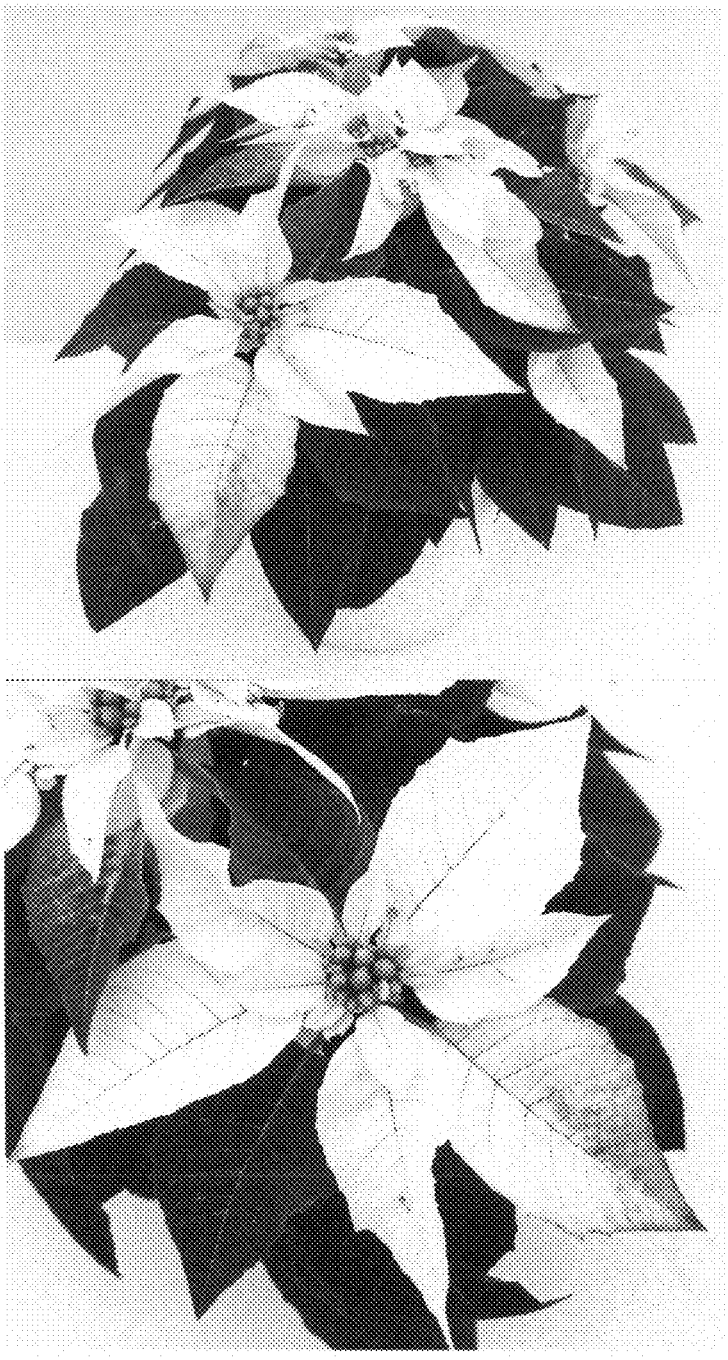

* * * * *